United States Patent [19]

Crugnola et al.

[11] Patent Number: 4,847,295
[45] Date of Patent: Jul. 11, 1989

[54] CYCLOALKYL-SUBSTITUTED 4-AMINOPHENYL HALO DERIVATIVES AND PROCESS FOR THEIR PREPARATION

[75] Inventors: Angelo Crugnola, Varese; Enrico di Salle; Paolo Lombardi, both of Milan, all of Italy

[73] Assignee: Farmitalia Carlo Erba S.r.l., Milan, Italy

[21] Appl. No.: 142,207

[22] Filed: Jan. 11, 1988

[30] Foreign Application Priority Data

Jan. 19, 1987 [GB] United Kingdom ............... 8701080

[51] Int. Cl.$^4$ .................... A61K 31/24; C07C 103/76
[52] U.S. Cl. .................... 514/538; 514/620; 514/646; 514/649; 560/47; 564/168; 564/366; 564/442
[58] Field of Search .................. 564/168, 366, 442; 560/47; 514/538, 620, 649, 646

[56] References Cited

U.S. PATENT DOCUMENTS 4,769,483  9/1988  Lombardi et al. ............... 564/168
4,797,411  1/1989  Crugnola et al. ............... 514/357

Primary Examiner—Bruce Gray
Attorney, Agent, or Firm—Armstrong, Nikaido, Marmelstein, Kubovcik & Murray

[57] ABSTRACT

The invention relates to cycloalkyl substituted 4-aminophenyl halo derivatives of formula (I)

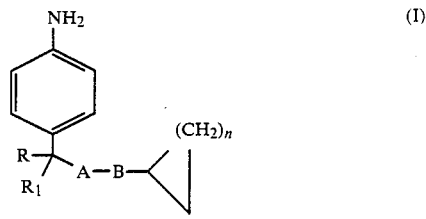

wherein
n is an integer of 1 to 5;
A is $>C=O$ or $-CH_2-$ and B is, independently, $-O-$, $-NH-$ or $-CH_2-$; and
either R is halogen and $R_1$ is unsubstituted $C_1-C_4$ alkyl; or R is hydrogen and $R_1$ is $C_1-C_4$ alkyl substituted by 1 to 4 halogen atoms,
including the pharmaceutically acceptable salts thereof. The compounds of the invention show aromatase inhibiting activity and can find use, for example, in the treatment of estrogen-dependent tumors and of prostatic hyperplasia.

7 Claims, No Drawings

CYCLOALKYL-SUBSTITUTED 4-AMINOPHENYL HALO DERIVATIVES AND PROCESS FOR THEIR PREPARATION

The present invention relates to cycloalkyl-substituted 4-aminophenyl halo derivatives, to a process for their preparation, to pharmaceutical compositions containing them and to the use of said compounds as inhibitors of the biosynthesis of estrogens, particularly as aromatase inhibitors.

Basic and clinical data indicate that estrogens are the hormones involved in the pathogenic cellular changes associated with the growth of some hormone-dependent cancers, such as breast, endometrial, ovarian and pancreatic carcinoma.

Estrogens are also involved in the pathogensis of prostatic hyperplasia. It has been envisaged that an effective inhibition of the biosynthesis of estrogens, better if resulting from compounds able to neutralize the activity of the enzyme aromatase which performs the aromatisation of the steroidic ring A, may be useful application for controlling the amount of circulating estrogens, and estrogen-dependent tumors.

Non-steroidal known substances which have been reported to be endowed with a more or less selective aromatase-inhibiting action are, for example, aminoglutethimide [Ann. Surg. 187, 475 (1978); Lancet, 2, 646 (1978)]; 4-cyclohexylaniline [Endocrinology, 114, 2128 (1984)], and 4-pyridyl-3-ethyl-2,6-piperidinedione [J. Med. Chem., 28, 200 (1985)].

The invention provides a new group of non-steroidal substances having aromatase-inhibiting properties, which are cycloalkyl-substituted 4-aminophenyl halo derivatives having the general formula (I)

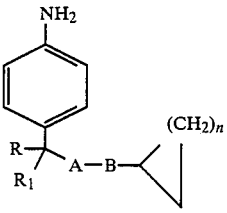

wherein
n is an integer of 1 to 5;
A is >C=O or —CH$_2$— and B is, independently, —O—, —NH— or —CH$_2$—; and
either R is halogen and R$_1$ is unsubstituted C$_1$–C$_4$ alkyl;
or R is hydrogen and R$_1$ is C$_1$–C$_4$ alkyl substituted by 1 to 4 halogen atoms.

Also the pharmaceutically acceptable salts of the compounds of formula (I) are included within the scope of the invention.

The said salts are the salts with pharmaceutically acceptable acids, both inorganic acids, such as, e.g., hydrochloric and sulfuric, and organic acids such as, e.g., citric, tartaric, maleic, malic, succinic, methanesulfonic and ethanesulfonic.

All the possible isomers of formula (I) are included within the scope of the invention, both separately and in mixture. Thus, for example, for each comound of formula (I) two distinct optical isomers, i.e. enantiomers, may exist according to the configuration of the chiral carbon atom carrying the R and R$_1$ substituents. The formula (I) is meant to cover both the enantiomers, either separately or in mixture.

Preferred enantiomers according to the invention are those represented by the formula (Ia)

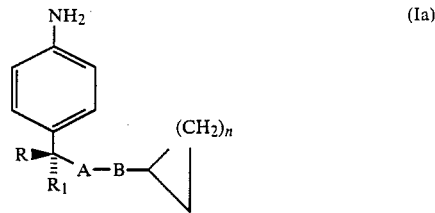

wherein n, A, B, R and R$_1$ are as defined above.

In the above formulae (I) and (Ia) a halogen atom is, preferably, F, Cl, Br, most preferably F.

A C$_1$–C$_4$ alkyl group is, preferably, methyl or ethyl, especially methyl.

A C$_1$–C$_4$ alkyl group substituted by 1 to 4 halogen atoms is, preferably, a methyl or ethyl group substituted by 1 to 3 halogen atoms, e.g. one of those hereinbefore specified, and it may be, in particular, a mono-, di-, or trifluoromethyl group, or 1-fluoroethyl or 1,2-difluoroethyl, most especially trifluoromethyl.

Preferred values for n are 3 and 4, in particular 4. Preferred salts are the hydrochlorides.

Examles of specific compounds preferred under this invention are the following compounds, both as single enantiomers and as mixtures of enantiomers, in particular racemic mixtures:

cyclohexyl 2-fluoro-2-(40'-aminophenyl)propionate;
cyclopentyl 2-fluoro-2-(4'-aminophenyl)propionate;
N-cyclohexyl-2-fluoro-2-(4'-aminophenyl)propanamide;
N-cyclopentyl-2-fluoro-2-(4'-aminophenyl)propanamide;
2-fluoro-2-(4'-aminophenyl)propylcyclohexyl ether;
2-fluoro-2-(4'-aminophenyl)propylcyclopentyl ether;
N-cyclohexyl-2-fluoro-2-(4'-aminophenyl)propylamine;
N-cyclopentyl-2-fluoro-2-(4'-aminophenyl)propylamine;
1-cyclohexyl-3-fluoro-3-(4'-aminophenyl)-2-butanone;
1-cyclopentyl-3-fluoro-3-(4'-aminophenyl)-2-butanone;
1-cyclohexyl-3-fluoro-3-(4'-aminophenyl)butane;
1-cyclopentyl-3-fluoro-3-(4'-aminophenyl)butane;
cyclohexyl 2-(4'-aminophenyl)-3,3,3-trifluoropropionate;
cyclopentyl 2-(4'-aminophenyl)-3,3,3-trifluoropropionate;
N-cyclohexyl-2-(4'-aminophenyl)-3,3,3-trifluoropropanamide;
N-cyclopentyl-2-(4'-aminophenyl)-3,3,3-trifluoropropanamide;
2-(4'-aminophenyl)-3,3,3-trifluoropropylcyclohexyl ether;
2-(4'-aminophenyl)-3,3,3-trifluoropropylcyclopentyl ether;
N-cyclohexyl-2-(4'-aminophenyl)-3,3,3-trifluoropropylamine;
N-cyclopentyl-2-(4'-aminophenyl)-3,3,3-trifluoropropylamine;
1-cyclohexyl-3-(4'-aminophenyl)-4,4,4-trifluoro-2-butanone;
1-cyclopentyl-3-(4'-aminophenyl)-4,4,4-trifluoro-2-butanone;

1-cyclohexyl-3-(4'-aminophenyl)-4,4,4-trifluorobutane; and 1-cyclopropyl-3-(4'-aminophenyl)-4,4,4-trifluorobutane, and the pharmaceutically acceptable salts thereof, especially the hydrochlorides.

The compounds of formula (I) may be prepared by a process comprising:

(1) reacting a compound of formula (II)

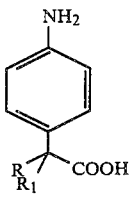
(II)

wherein R and R₁ are as defined above, or a reactive derivative thereof, with a compound of formula (III)

(III)

wherein n is as defined above and X is OH or NH₂, so obtaining a compound of formula (I) wherein R, R₁ and n are as defined above, A is >C=O and B is —O— or —NH— respectively; or (2) reducing a compound of formula (I) wherein R, R₁ and n are as defined above and A is >C=O and B is —O', —NH—, or —CH₂—, so obtaining a corresponding compound of formula (I) wherein A is —CH₂— and B is —O—, —NH— or —CH₂—; or (3) reducing a compound of formula (IV)

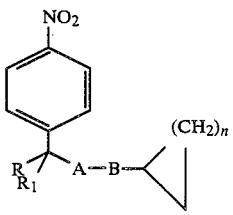
(IV)

wherein
R, R₁ and n are as defined above,
A is >C=O or —CH₂— and B is, independently, —O—, —NH— or —CH₂—, so obtaining a corresponding compound of formula (I) wherein R, R₁ and n are as defined above,
A is >C=O or —CH₂— and B is, independently, —O—, —NH— or —CH₂—, and if desired, salifying the compound of formula (I) or obtaining a free compound of formula (I) from a salt thereof and/or, if desired, separating a mixture of isomers of formula (I) into the single isomers.

The intermediate compounds of the above formulae (II) and (IV) and of the following formula (V) may be, as the compounds of formula (I), either single enantiomers or mixtures of enantiomers.

A reactive derivative of an aminoacid of formula (II) may be, e.g., an acyl halide, in particular the chloride, of the acid, or the anhydride thereof.

Preferably the reaction between a compound of formula (II) and a compound of formula (III), is performed using a reactive derivative of the compound (II), e.g. of the kind previously specified, and then the reaction is preferably carried out in an inert organic solvent such as, for instance, anhydrous benzene or toluene, in the presence of a base, either an organic base such as, e.g., triethylamine or pyridine, or an inorganic base such as, e.g., an alkali metal, e.g. sodium or potassium, hydroxide, carbonate or bicarbonate.

Usual procedures described in organic chemistry for esterification and amidation reactions may be followed. The reduction of a compound of formula (I) wherein A is >C=O and B is —O— or —NH— is carried out in presence of a reducing agent such as, e.g., a hydride, for instance, LiAlH₄ or B₂H₆, in an inert solvent such as tetrahydrofuran, dioxane, diglyme and similar solvents, preferably at a temperature ranging between about 40° C. and about 120° C. for a reaction time varying approximately in the range of 4–48 hours.

The reduction of a compound of formula (I) wherein A is >C=O and B is —CH₂— may be, e.g., carried out by transforming the carbonyl group into the corresponding 1,3-dithiolane according to general methods, and then reducing the latter derivative by the action of an alkali metal, such as, e.g., lithium, sodium or calcium, dissolving in liquid ammonia, according to known procedures. Alternatively, the 1,3-dithiolane derivative may be reduced by Raney-Nickel in an inert solvent, such as, e.g., ethanol, dioxane, acetone, at a temperature ranging between about 20° C. and about 80° C. for a reaction time of about 0.5–4 hours, or also by tributyl tin hydride in an inert aprotic solvent, preferably benzene, at a temperature ranging between about 60° C. and about 100° C., for a reaction time of about 1–3 hours. Optionally, the carbonyl group in the compound of formula (I) may be transformed into the corresponding tosylhydrazone by general methods and the derivative so obtained may be reduced by the action of hydrides, for instance with lithium aluminium hydride or bis(benzyloxy)borane, operating in an inert, aprotic solvent such as, e.g., diethylether, dioxane, tetrahydrofuran, diglyme, chloroform or methylene chloride, at a temperature ranging between about 0° C. and around 40° C. and for reaction times of about 0.5–4 hours; or with sodium cyanoborohydride operating in a protic solvent such as, e.g., methanol, ethanol, or propanol, at a temperature ranging between around 40° C. and around 100° C. for a reaction time of about 1–24 hours.

The reduction of a compound of formula (IV) may be carried out, for instance, by stannous chloride in an inert solvent such as, e.g., methanol, ethanol or ethyl acetate at a temperature ranging between about 40° C. and about 100° C. for a reaction time of about 0.5–3 hours; or by ammonium formate in presence of a hydrogenation catalyst, preferably 10% Pd/C operating in a suitable solvent such as, e.g., an aliphatic alcohol; e.g. methanol or ethanol, preferably at a temperature ranging between about 20° C. and about 50° C. in a reaction time of from about 0.5 hour to about 1 hour; or by hydrogenation in presence of a catalyst, preferably 10% Pd/C, in a solvent such as, e.g., an aliphatic alcohol, in particular methanol or ethanol, at a temperature ranging between about 20° C. and about 50° C. and at a pressure ranging approximately between the atmospheric pressure and 50 psi. The optional salification of a compound of formula (I) and the preparation of a free compound of formula (I) from a salt thereof may be performed by conventional known methods. Standard procedures may be followed also for separating a mixture of isomers into the single isomers, in particular, for example, for separating a racemic mixture into the single enantiomers.

The compounds of formula (II) and (III) are either known compounds or may be prepared by known methods from known compounds. Also the compounds of formula (IV) are either known compounds or can be prepared from known compounds following methods and procedures known in the organic chemistry.

In particular, for example, a compound of formula (IV) wherein A is $>C=O$ and B is $-O-$ or $-NH-$ can be prepared reacting a compound of formula (V)

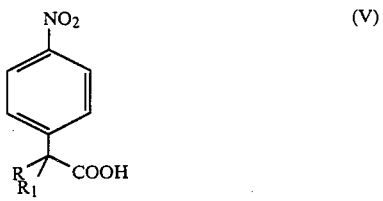

wherein R and $R_1$ are as defined above or, preferably, a reactive derivative thereof such as, for instance, a corresponding acyl halide, e.g. chloride, or the anhydride thereof, with a compound of formula (III) as previously defined. The reaction may be performed under conditions analogous to those reported before in this specification for the reaction between a compound of formula (II) and a compound of formula (III).

A compound of formula (IV) wherein A is $>C=O$ and B is $-CH_2-$ may be prepared, e.g., reacting a compound of formula (V), or a reactive derivative thereof as hereinbefore defined, with a compound of formula (VI)

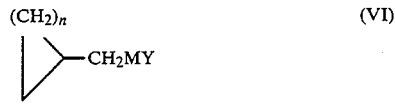

wherein n is as defined above, M is a metal, preferably Mg, suitable to give a Grignard reagent, and Y is a halogen, preferably bromine, iodine or chlorine.

The reaction may be carried out in the usual conditions described in the organic chemistry for the Grignard reactions.

The compounds having the formulae (V) and (VI) are known compounds or may be prepared by known methods from known compounds. The compounds of the invention show aromatase inhibiting activity.

A comparison between their in vitro aromatase inibitory effect and the effect of the well-known non-steroidal aromatase inhibitors aminoglutethimide [R. J. Santen et al., Cancer Research (Suppl.) 42, 3353s, 1982] and 4-cyclohexyl-aniline [J. T. Kellis et al., Endocrinology 114, 2128, 1984] indicates, in fact, that the compounds of the invention are more potent aromatase inhibitors than the reference compounds. In particular, for example, the comparison between the in vitro activity of the compound of the invention N-cyclohexyl-2-(4'-aminophenyl)-3,3,3-trifluoropropanamide [internal code FCE 25331] and the two above said reference compounds gave the results summarized in the following table.

TABLE

| Inhibition of human placental aromatase in vitro | | |
|---|---|---|
| Compound | $IC_{50}$ ($\mu M$) | Relative potency |
| Aminoglutethimide | 2.12 | 1 (by definition) |
| 4-cyclohexylaniline | 1.22 | 1.7 |
| FCE 25331 | 0.33 | 6.4 |

FCE 25331: I, R = H, $R_1$ = $CF_3$, A = $>C=O$, B = $-NH-$, n = 4.

The assay of the aromatase inhibition in vitro was carried out as follows: the enzyme system was isolated from the microsomal fraction of human placental tissue according to standard procedure. The assay of Thompson and Silteri [F. A. Thompson and P. K. Silteri, J. Biol. Chem. 249, 5364, 1974] which determines the rate of aromatization as measured by the liberation of $^3H_2O$ from 4-[1$\beta$, 2$\beta$-$^3$H]androstene-3,17-dione was used.

All incubations were carried out in a shaking water bath at 37° C. in air in 10 mM potassium phosphate buffer, pH 7.5, which contained 100 mM Kcl, 1 mM EDTA and 1 mM dithiothreitol. The experiments were carried out in 1 ml incubation volume containing 50 nM 4-[$^3$H]androstenedione, various concentrations of the inhibitors. 100 $\mu$m NADPH and 0.05 mg of microsomal proteins. After 15 minutes of incubation the reaction was stopped by the addition of chloroform (5 ml).

After centrifugation at 1500 xg for 5 minutes, aliquots (0.5 ml) were removed from the water phase for determination of $^3H_2O$ formed.

The concentration of each compound required to reduce control aromatase by 50% ($IC_{50}$) was determined by plotting % inhibition versus log of inhibitor concentration.

The relative potency of each compound versus aminoglutethimide was calculated according to the relation:

$$\text{Relative potency} = \frac{IC_{50} \text{ of aminoglutethimide}}{IC_{50} \text{ of test compound.}}$$

By virtue of their ability to inhibit aromatase and, consequently, to reduce estrogen levels, the compounds of the invention can find use in the treatment and prevention of various estrogen dependent diseases, e.g. estrogen dependent tumors, for instance breast, endometrial, ovarian and pancreatic cancers; gynecomastia; benign breast disease; endometriosis; polycystic ovarian disease, and precocious puberty. Another application of the compounds of the invention is in the therapeutic and/or prophylactic treatment of prostatic hyperplasia, a disease of the estrogen dependent stromal tissue.

The compounds of the invention can be useful also for the treatment of male infertility associated with oligospermia and for female fertility control, by virtue of their ability to inhibit ovulation and egg nidation.

Accordingly, object of the invention is also a method of producing inhibition of the enzyme aromatase and, consequently, because of inhibition of estrogen biosynthesis, a method of treating estrogen dependent deseases, e.g. those mentioned above, in a patient in need of it, which method comprises administering to the patient an effective amount of a compound of the invention or a pharmaceutical composition containing it.

The compounds of the invention can be administered in a variety of dosage forms, e.g., orally, in the form of tablets, capsules, sugar or film coated tablets, liquid solutions or suspensions; rectally, in the form of suppositories; parenterally, e.g. intramuscularly, or by intravenous injection or infusion.

The dosage depends on the age, weight, conditions of the patient and administration route; for example the dosage adopted for oral administration to adult humans may range from about 10 to about 400 mg pro dose, from 1 to 5 times daily.

As already said the invention includes pharmaceutical compositions comprising a compound of the invention in association with a pharmaceutically acceptable excipient (which can be a carrier or diluent). The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, aliginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol. The supsensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions. The suppositories may contain together with the active compound a pharmaceutically accpetable carrier, e.g. cocoa-butter, polyethylene glycol, a polyoxyethylene sorbitan fatty acid ester surfactant or lecithin. The following examples illustrate but do not limit the invention.

When the configuration is unspecified, the compounds are meant to be racemic compounds, i.e. racemates.

EXAMPLE 1

Cyclohexyl 2-fluoro-2-(4'-aminophenyl)propionate [I, R=—F, $R_1$=—$CH_3$, A=>C=O, B=—O—, n=4]

To a stirred suspension of 2-fluoro-2-(4-aminophenyl)propionic acid (9.15 g, 50 mmole) in dry benzene (100 ml) is added thionyl chloride (30 ml). The resulting mixture is refluxed for 4 hours, cooled and evaporated in vacuo to yield a brown oil.

The acyl chloride so obtained, dissolved in dry benzene (50 ml) is then added dropwise to a stirred solution of cyclohexanol (5 g, 50 mmole) and triethylamine (35 ml, 250 mmole) in dry benzene (100 ml) at 5°-10° C. After 3 hrs of additional stirring at room temperature, the reaction mixture is poured into a cold 10% $Na_2CO_3$ aqueous solution, the organic phase is separated, washed with water, dried over $Na_2SO_4$, filtered and concentrated in vacuo. The resulting residue is purified by fractional distillation. There are obtained 7.90 g of the title compound.

IR ($CHCl_3$, $cm^{-1}$): 3460, 3380, 3100, 2980, 2940, 2860, 1720, 1620, 1510.

In analogous fashion one can prepare the single enantiomers of the above title compound as well as the following compounds both as racemates and as single enantiomers:

cyclopentyl 2-fluoro-2-(4'-amionophenyl)propionate;
cyclopropyl 2-fluoro-2-(4'-aminophenyl)propionate;
cyclohexyl 2-chloro-2-(4'-aminophenyl)propionate;
cyclohexyl 2-bromo-2-(4'-aminophenyl)propionate, and
cyclohexyl 2-fluoro-2-(4'-aminophenyl)butanoate.

EXAMPLE 2

N-cyclohexyl-2-fluoro-2-(4'-aminophenyl)propanamide [I, R=—F, $R_1$=—$CH_3$, A=>C=O, B=—NH—, n=4]

The acyl chloride, prepared from 1.85 g of 2-fluoro-2-(4'-aminophenyl)propionic acid and 6 ml of thionyl chloride as reported in the Example 1, is dissolved in dry benzene (15 ml) and added dropwise to a stirred solution of cyclohexylamine (3 g, 30 mmole) in dry benzene (30 ml) at 5°-10° C. After 3 hrs of additional stirring at room temperature the reaction mixture is worked up as reported in the Example 1. The crude product is purified by flash column chromatography on silica gel eluting with chloroform:methanol 98:2 and by recrystallisation from benzene:n-hexane 1:1. There are obtained 1.50 g of the title compound, IR (KBr, $cm^{-1}$): 3600-3100, 3040, 3010, 2920, 2840, 1635. In analogous fashion one can prepare the single enantiomers of the above title compound as well as the following compounds both as racemates and as single enantiomers:

N-cyclopentyl-2-fluoro-2-(4'-aminophenyl)propanamide;
N-cyclopentyl-2-fluoro-2-(4'-aminophenyl)propanamide;
N-cyclopentyl-2-chloro-2-(4'-aminophenyl)propanamide;
N-cyclopentyl-2-chloro-2-(4'-aminophenyl)propanamide;
N-cyclopropyl-2-chloro-2-(4'-aminophenyl)propanamide;
N-cyclohexyl-2-bromo-2-(4'-aminophenyl)propanamide;
N-cyclopentyl-2-bromo-2-(4'-aminophenyl)propanamide;
N-cyclohexyl-2-fluoro-2-(4'-aminophenyl)butanamide;
N-cyclohexyl-2-chloro-2-(4'-aminophenyl)butanamide, and
N-cyclohexyl-2-bromo-2-(4'-aminophenyl)butanamide.

EXAMPLE 3

Cyclohexyl 2-(4'-aminophenyl)-3,3,3-trifluoropropionate [I, R=—H, R=—CF$_3$, A=>C=O, B=—O—, n=4]

The title compound is prepared in 62% yield starting from 2-(4'-aminophenyl)-3,3,3-trifluoropropionic acid (8.76 g, 40 mmole) and cyclohexanol (4 g, 40 mmole) with a procedure similar to the one described in the Example 1, IR (CHCl$_3$, cm$^{-1}$): 3450, 3375, 3150, 1720, 1620, 1515. In analogous fashion one can prepare the single enantiomers of the above title compound as well as the following compounds both as racemates and as single enantiomers:
cyclohexyl 2-(4'-aminophenyl)-3-fluoropropionate;
cyclopentyl 2-(4'-aminophenyl)-3,3,3-trifluoropropionate, and
cyclopentyl 2-(4'-aminophenyl)-3-fluoropropionate.

EXAMPLE 4

N-cyclohexyl-2-(4'-aminophenyl)-3,3,3-trifluoropropanamide [I, R=—H, R$_1$=—CF$_3$, A=>C=O, B=—NH—, n=4]

The title compound is prepared in 51% yield starting from 2-(4'-aminophenyl)-3,3,3-trifluoropropionic acid (4.38 g, 20 mmole) and cyclohexylamine (4 g, 40 mmole) with a procedure similar to the one described in the Example 2, m.p. 143°–146° C., Elemental analysis: calculated % (found %): C 59.93 (59.75), H 6.38 (6.35), N 9.33 (9.23), F 18.98 (18.71).

NMR (CDCl$_3$, δ): 0.8–2.0 (10H, m), 2.20 (2H, br), 3.78 (1H, m), 3.95 (1H, q), 5.40 (1H, br), 6.68 (2H, m), 7.71 (2H, m).

IR (KBr, cm$^{-1}$): 3440, 3060, 1645, 1540, 1510.

In analogous fashion one can prepare the single enantiomers of the above title compound as well as the following compounds both as racemates and as single enantiomers:
N-cyclohexyl-2-(4'-aminophenyl)-3,3-difluoropropanamde;
N-cyclohexyl-2-(4'-aminophenyl)-3-fluoropropanamide;
N-cyclohexyl-2-(4'-aminophenyl)-3,3,3-trichloropropanamide;
N-cyclohexyl-2-(4'-aminophenyl)-3,3-dichloropropanamide;
N-cyclohexyl-2-(4'-aminophenyl)-3-chloropropanamide;
N-cyclohexyl-2-(4'-aminophenyl)-3,3-difluorobutanamide;
N-cyclohexyl-2-(4'-aminophenyl)-3-fluorobutanamide;
N-cyclohexyl-2-(4'-aminophenyl)-4,4-difluorobutanamide;
N-cyclohexyl-2-(4'-aminophenyl)-4,4,4-trifluorobutanamide;
N-cyclohexyl-2-(4'-aminophenyl)-4,4-difluorobutanamide;
N-cyclohexyl-2-(4'-aminophenyl)-4-fluorobutanamide;
N-cyclohexyl-2-(4'-aminophenyl)-3,3,3-trifluoropropanamide;
N-cyclopentyl-2-(4'-aminophenyl)-3,3-difluoropropanamide;
N-cyclopentyl-2-(4'-aminophenyl)-3-fluoropropanamide;
N-cyclopentyl-2-(4'-aminophenyl)-3,3-difluorobutanamide;
N-cyclopentyl-2-(4'-aminophenyl)-3-fluorobutanamide;
N-cyclopentyl-2-(4'-aminophenyl)-3,4-difluorobutanamide;
N-cyclopentyl-2-(4'-aminophenyl)-4,4,4-trifluorobutanamide;
N-cyclopentyl-2-(4'-aminophenyl)-4,4-difluorobutanamide, and
N-cyclopentyl-2-(4'-aminophenyl)-4-fluorobutanamide.

EXAMPLE 5

2-fluoro-2-(4'-aminophenyl)propylcyclohexyl ether [I, R=—F, R$_1$=—CH$_3$, A=—CH$_2$—, B=—O—, n=4]

To a stirred suspension of lithium aluminum hydride (2.5 g) in anhydrous tetrahydrofuran (50 ml) is added a mixture of cyclohexyl 2-fluoro-2-(4'-aminophenyl)propionate (3.98 g, 15 mmole), prepared as described in the Example 1, and borontrifluoride etherate (30 ml) in anhydrous tetrahydrofuran (50 ml) dropwise with external cooling. After 3 hrs at 45° C., the reaction mixture is carefully decomposed by adding water, followed by a 23% hydrochloride acid solution. Most of the organic solvent is evaporated in vacuo, the aqueous solution is brought to pH 9 by adding a concentrated sodium hydroxide solution and extracted with diethyl ether (3 times). The combined extracts are washed with water to neutral, dried over Na$_2$SO$_4$ and evaporated in vacuo. The resulting residue is purified by column chromatography on silica gel eluting with benzene:ethyl acetate 95:5 and by fractional distillation. There are obtained 2.5 g of the title compound.

IR (CHCl$_3$, cm$^{-1}$): 3440, 3360, 3080, 3020, 2920, 2840, 1610, 1510, 1175, 1130, 1075.

In analogous fashion one can prepare the single enantiomers of the above title compound as well as the following compounds both as racemates and as single enantiomers:
2-fluoro-2-(4'-aminophenyl)propylcyclopentyl ether;
2-(4'-aminophenyl)-3,3,3-trifluoropropylcyclohexyl ether, and
2-(4'-aminophenyl)-3,3,3-trifluoropropylcyclopentyl ether.

EXAMPLE 6

N-cyclohexyl-2-fluoro-2-(4'-aminophenyl)propylamine bis hydrochloride [I, R=—F, R$_1$=—CH$_3$, A=—CH$_2$—, B=—NH—, n=4]

To a stirred suspension of lithium aluminum hydride (0.4 g) in anhydrous diglyme (10 ml) is added N-cyclohexyl 2-fluoro-2-(4'-aminophenyl)propanamide (0.518 g, 2 mmole), prepared as described in Example 2, dissolved in anhydrous diglyme (5 ml) dropwise and under nitrogen atmosphere.

The reaction mixture is then heated at 85°–95° C. for 6 hrs. After cooling, the excess of lithium aluminum hydride is decomposed by the careful addition of a mixture of methanol, t-butylmethylether and water. The organic phase is separated, washed with water, dried over Na$_2$SO$_4$ and filtered. The filtrate is saturated with anhydrous hydrogen chloride and the resulting precipitate is filtered off and recrystallized from methanol:isopropanol 1:2. There are obtained 0.55 g of the title compound as bis hydrochloride.

IR (KBr, cm$^{-1}$): 3100–2300, 2920, 2840, 1610, 1505, 1450, 1375.

In analogous fashion one can prepare the single enantiomers of the above title compound as well as the following compounds both as racemates and as single enantiomers:

N-cyclopentyl-2-fluoro-2-(4'-aminophenyl)propylamine;
N-cyclohexyl-2-(4'-aminophenyl)-3,3,3-trifluoropropylamine, and
N-cyclopentyl-2-(4'-aminophenyl)-3,3,3-trifluoropropylamine.

EXAMPLE 7

1-cyclohexyl-3-fluoro-3-(4'-aminophenyl)butane [I, R=—F, $R_1$=—$CH_3$, A=B=—$CH_2$—, n=4]

To a solution of 1-cyclohexyl-3-fluoro-3-(4'-aminophenyl)-2-butanone (2.63 g, 10 mmole) in methylene chloride (50 ml) there are added ethanedithiol (2 ml) and boron trifluoride etherate (2 ml). The mixture is stirred at room temperature during 2 hours, then it is washed with water, a 8% $NaHCO_3$ aqueous solution and water, then dried over $CaCl_2$, filtered and evaporated in vacuo. The crude thioketal so obtained (3.3 g) is dissolved in anhydrous tetrahydrofuran (30 ml) and stirred in presence of Raney nickel (10 g) (prepared according to Org. Synth., 3, 181) for 2 hours at room temperature. The catalyst is filtered off and washed with methylene chloride. The combined filtrate and washings are evaporated in vacuo to yield a residue which is purified by fractional distillation.

There are obtained 1.5 g of the title compound, IR ($CHCl_3$, $cm^{-1}$): 3440, 3360, 3080, 3020, 2920, 2840, 1610, 1510.

In analogous fashion one can prepare the single enantiomers of the above title compound as well as the following compounds both as racemates and as single enantiomers:
1-cyclopentyl-3-fluoro-3-(4'-aminophenyl)butane;
1-cyclohexyl-3-(4'-aminophenyl)-4,4,4-trifluorobutane, and
1-cyclopentyl-3-(4'-aminophenyl)-4,4,4-trifluorobutane.

EXAMPLE 8

1-cyclohexyl-3-fluoro-3-(4'-nitrophenyl)-2-butanone [IV, R=—F, $R_1$=—$CH_3$, A=>C=O, B=—$CH_2$—, n=4]

To a stirred solution of cyclohexylmethyl magnesium iodide (prepared from 7.5 g of cyclohexylmethyl iodide and 0.7 g of magnesium turnings) in anhydrous diethyl ether (30 ml) cooled at 0° C. there is added pulverized anhydrous cadmium chloride (2.6 g) in small portions over a period of 45 min. After one hour of additional stirring at room temperature, the resulting solution is cooled at −70° C. and treated with the dropwise addition of 2-fluoro-2-(4'-nitrophenyl)propionyl chloride (prepared from 4.26 g, 20 mmole, of 2-(4'-nitrophenyl)-propionic acid and 8.0 ml of thionyl chloride) in anhydrous diethyl ether (10 ml). After one hour of additional stirring, the reaction mixture is carefully decomposed by the dropwise addition of 50 ml of water. The organic phase is separated, the aqueous phase is extracted with diethylether (3 times), the combined extracts are dried over $Na_2SO_4$, filtered and concentrated in vacuo. There are obtained 4.6 g of the crude title compound.

IR ($CHCl_3$, $cm^{-1}$): 1715, 1520, 1350.

In analogous fashion one can prepare the single enantiomers of the above title compound as well as the following compounds both as racemates and as single enantiomers:
1-cyclopentyl-3-fluoro-3-(4'-nitrophenyl)-2-butanone;
1-cyclohexyl-3-(4'-nitrophenyl)-4,4,4-trifluoro-2-butanone, and
1-cyclopentyl-3-(4'-nitrophenyl)-4,4,4-trifluoro-2-butanone.

EXAMPLE 9

1-cyclohexyl-3-fluoro-3-(4-aminophenyl)-2-butanone [I, R=—F, $R_1$=—$CH_3$, A=>C=O, B=—$CH_2$—, n=4]

A stirred mixture of 4.0 g of crude 1-cyclohexyl-3-fluoro-3-(4'-nitrophenyl)-2-butanone and 400 mg of 10% Pd/C Catalyst in 75 ml of 95% ethanol is hydrogenated in a Brown-type hydrogenator at room temperature till the uptake of hydrogen ceased. The catalyst is filtered off and the filtrate is evaporated in vacuo. The resulting residue is purified by fractional distillation. There are obtained 1.36 g of the title compound, IR ($CHCl_3$, $cm^{-1}$): 3460, 3380, 3020, 2920, 2850, 1210, 1620, 1510.

In analogous fashion one can prepare the single enantiomers of the above title compound as well as the following compounds both as racemates and as single enantiomers:
1-cyclopentyl-3-fluoro-3-(4'-aminophenyl)-2-butanone;
1-cyclohexyl-3-(4'-aminophenyl)-4,4,4-trifluoro-2-butanone, and 1-cyclopentyl-3-(4'-aminophenyl)-4,4,4-trifluoro-2-butanone.

EXAMPLE 10

Tablets, each weighing 0.150 g and containing 25 mg of the active substance, can be manufactured as follows:

| Composition (for 10,000 tablets) | |
|---|---|
| N—cyclohexyl-2-fluoro-2-(4'-aminophenyl)propanamide | 250 g |
| Lactose | 800 g |
| Corn starch | 415 g |
| Talc powder | 30 g |
| Magnesium stearate | 5 g |

The N-cyclohexyl-2-fluoro-2-(4'-aminophenyl)-propanamide, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 11

Capsules, each dosed at 0.200 g and containing 20 mg of the active substance can be prepared as follows:

| Composition for 500 capsules: | |
|---|---|
| N—cyclohexyl-2-(4'-aminophenyl)-3,3,3-trifluoropropanamide | 10 g |
| Lactose | 80 g |
| Corn starch | 5 g |
| Magnesium stearate | 5 g |

This formulation can be encapsulated in two-piece hard gelatin capsules and dosed at 0.200 g for each capsule.

We claim:

1. A cycloalkyl-substituted 4-aminophenyl halo derivative of formula (I)

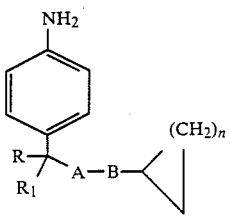

(I)

wherein
n is an integer of 1 to 5;
A is >C=O or —CH₂— and B is, independently, —O—, —NH— or —CH₂—; and
either R is halogen and R₁ is unsubstituted C₁–C₄ alkyl; or R is hydrogen and R₁ is C₁–C₄ alkyl substituted by 1 to 4 halogen atoms and the pharmaceutically acceptable salts thereof.

2. A compound according to claim 1, wherein the cycloalkyl-substituted 4-aminophenyl halo derivative is the enantiomer having the formula (Ia)

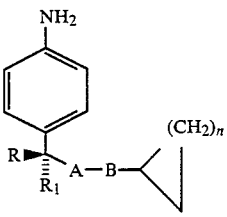

(Ia)

wherein
n, A, B, R and R₁ are as defined in claim 1.

3. A compound according to claim 1 or 2, wherein n is 3 or 4.

4. A compound, either as single enantiomer or as racemic mixture, selected from the group consisting of:
cyclohexyl 2-fluoro-2-(4'-aminophenyl)propionate;
cyclopentyl 2-fluoro-2-(4'-aminophenyl)propionate;
N-cyclohexyl-2-fluoro-2-(4'-aminophenyl)propanamide;
N-cyclopentyl-2-fluoro-2-(4'-aminophenyl)propanamide;
2-fluoro-2-(4'-aminophenyl)propylcyclohexyl ether;
2-fluoro-2-(4'-aminophenyl)propylcyclopentyl ether;
N-cyclohexyl-2-fluoro-2-(4'-aminophenyl)propylamine;
N-cyclopentyl-2-fluoro-2-(4'-aminophenyl)propylamine;
1-cyclohexyl-3-fluoro-3-(4'-aminophenyl)-2-butanone;
1-cyclopentyl-3-fluoro-3-(4'-aminophenyl)-2-butanone;
1-cyclohexyl-3-fluoro-3-(4'-aminophenyl)butane;
1-cyclopentyl-3-fluoro-3-(4'-aminophenyl)butane;
cyclohexyl 2-(4'-aminophenyl)-3,3,3-trifluoropropionate;
cyclopentyl 2-(4'-aminophenyl)-3,3,3-trifluoropropionate;
N-cyclohexyl-2-(4'-aminophenyl)-3,3,3-trifluoropropanamide;
N-cyclopentyl-2-(4'-aminophenyl)-3,3,3-trifluoropropanamide;
2-(4'-aminophenyl)-3,3,3-trifluoropropylcyclohexyl ether;
2-(4'-aminophenyl)-3,3,3-trifluoropropylcyclopentyl ether;
N-cyclohexyl-2-(4'-aminophenyl)-3,3,3-trifluoropropylamine;
N-cyclopentyl-2-(4'-aminophenyl)-3,3,3-trifluoropropylamine;
1-cyclohexyl-3-(4'-aminophenyl)-4,4,4-trifluoro-2-butanone;
1-cyclopentyl-3-(4'-aminophenyl)-4,4,4-trifluoro-2-butanone;
1-cyclohexyl-3-(4'-aminophenyl)-4,4,4-trifluorobutane; and
1-cyclopentyl-3-(4'-aminophenyl)-4,4,4-trifluorobutane,
and the pharmaceutically acceptable salts thereof.

5. A salt of a compound of claim 4 wherein the salt is the hydrochloride.

6. A compound according to claim 1, wherein said compound is N-cyclohexyl-2-(4'-aminophenyl)-3,3,3-trifluoropropanamide.

7. A pharmaceutical composition comprising an inert carrier and/or diluent and, as the active substance, an effective amount of a compound of formula (I) according to claim 1 or a pharmaceutically acceptable salt thereof.

* * * * *